US010327980B1

(12) United States Patent
Termanini et al.

(10) Patent No.: US 10,327,980 B1
(45) Date of Patent: Jun. 25, 2019

(54) FACIAL ROLLER MASSAGER

(71) Applicants: Zafer Termanini, Port Saint Lucie, NJ (US); Klara Termanini, Port Saint Lucie, FL (US)

(72) Inventors: Zafer Termanini, Port Saint Lucie, NJ (US); Klara Termanini, Port Saint Lucie, FL (US)

( * ) Notice: Subject to any disclaimer, the term of this patent is extended or adjusted under 35 U.S.C. 154(b) by 0 days.

(21) Appl. No.: 15/984,398

(22) Filed: May 20, 2018

(51) Int. Cl.
*A61H 15/00* (2006.01)
*A61N 1/30* (2006.01)
*A61N 1/00* (2006.01)
*A61N 1/04* (2006.01)

(52) U.S. Cl.
CPC ..... *A61H 15/0085* (2013.01); *A61H 15/0092* (2013.01); *A61N 1/00* (2013.01); *A61N 1/0404* (2013.01); *A61N 1/303* (2013.01); *A61H 2015/0007* (2013.01); *A61H 2015/0014* (2013.01); *A61H 2015/0021* (2013.01); *A61H 2015/0028* (2013.01); *A61H 2015/0042* (2013.01); *A61H 2201/1215* (2013.01); *A61H 2201/1463* (2013.01); *A61H 2201/1671* (2013.01); *A61H 2201/5043* (2013.01); *A61H 2205/022* (2013.01)

(58) Field of Classification Search
CPC ........ A61H 15/0085; A61H 2201/1215; A61H 2201/5043; A61H 2201/1463; A61H 2015/0021; A61H 2205/022; A61H 2201/1671; A61H 15/00; A61H 2015/0007; A61H 2015/0014; A61H 2015/0028; A61H 2015/0035; A61H 2015/0042; A61H 2015/005; A61H 2015/0057; A61H 2015/0064; A61H 2015/0071; A61H 15/0078; A61H 15/02; A61H 2201/0107; A61H 2201/0153; A61H 2201/0157; A61H 2201/0161; A61H 2201/1223; A61N 1/328; A61N 1/327; A61N 1/322; A61N 1/303; A61N 1/18; A61N 1/20; A61N 1/205; A61N 1/22; A61N 1/24; A61N 1/26; A61N 1/28; A61N 1/30; A61N 1/306; A61N 1/0404

See application file for complete search history.

(56) References Cited

U.S. PATENT DOCUMENTS

| | | | | | |
|---|---|---|---|---|---|
| 374,747 | A | * | 12/1887 | Muir | 601/20 |
| 407,071 | A | * | 7/1889 | Hopkins | A61H 15/0085 601/113 |
| 564,258 | A | * | 7/1896 | Rossbach | 601/20 |
| 637,321 | A | * | 11/1899 | Casper | 601/20 |

(Continued)

FOREIGN PATENT DOCUMENTS

GB 2261377 A * 5/1993 ............... A61N 1/26

*Primary Examiner* — Michael J Tsai
*Assistant Examiner* — Tu A Vo
(74) *Attorney, Agent, or Firm* — Samir Termanini, Esq.

(57) ABSTRACT

Hand held unit for providing rollers used for massaging the facial skin and muscles. Said rollers rotate vertically providing deep thumping massage for the facial skin and muscles. Interchangeable Conductive rollers provide horizontal massaging effect as well as benefit of iontophoresis microcurrent for purpose of introducing into the skin stem cell solutions and other cosmotological products. Power supply unit will provide appropriate oscillating microcurrent as well as the power for the motor.

4 Claims, 7 Drawing Sheets

(56) References Cited

U.S. PATENT DOCUMENTS

| | | | | |
|---|---|---|---|---|
| 693,063 | A * | 2/1902 | Preston | 601/20 |
| 835,082 | A * | 11/1906 | Schmidt | 601/20 |
| 852,163 | A * | 4/1907 | Buchanan | 361/232 |
| 872,148 | A * | 11/1907 | Raymond et al. | H01M 2/0275 |
| | | | | 429/164 |
| 917,367 | A * | 4/1909 | Scott et al. | 200/60 |
| 942,976 | A * | 12/1909 | Reach | A61H 15/00 |
| | | | | 601/113 |
| 1,049,759 | A * | 1/1913 | Oliver | 200/6 R |
| 1,055,236 | A * | 3/1913 | Seacombe | 200/19.18 |
| 1,059,090 | A * | 4/1913 | Tibbals | 336/145 |
| 1,064,093 | A * | 6/1913 | Schulze | A61H 15/0085 |
| | | | | 601/113 |
| 1,070,924 | A * | 8/1913 | Schulze | A61H 15/0085 |
| | | | | 601/113 |
| 1,103,669 | A * | 7/1914 | Gibbs | 601/119 |
| 1,173,838 | A * | 2/1916 | Miller | A61H 15/0085 |
| | | | | 601/113 |
| 1,289,864 | A * | 12/1918 | Modern | 336/136 |
| 1,433,184 | A * | 10/1922 | Csanyi | A61N 1/322 |
| | | | | 336/107 |
| 1,532,463 | A * | 4/1925 | Winterfield | A61N 1/26 |
| | | | | 336/66 |
| 1,557,417 | A * | 10/1925 | Cheney | A61H 15/0085 |
| | | | | 185/40 S |
| 1,567,741 | A * | 12/1925 | Lloyd | A61H 15/0092 |
| | | | | 200/19.13 |
| 1,577,751 | A * | 3/1926 | Paschall | A61H 7/004 |
| | | | | 15/22.1 |
| 1,631,792 | A * | 6/1927 | Burnley | A61H 15/0085 |
| | | | | 601/112 |
| 1,645,339 | A * | 10/1927 | Monroe | 601/116 |
| 1,655,554 | A * | 1/1928 | Lev | A61N 1/08 |
| | | | | 336/107 |
| 1,710,051 | A * | 4/1929 | Giacopazzi | A61H 15/0085 |
| | | | | 601/123 |
| 1,789,758 | A * | 1/1931 | Kays | A61H 15/0092 |
| | | | | 307/132 V |
| 1,899,208 | A * | 2/1933 | Murphy | A61H 15/0085 |
| | | | | 601/113 |
| 2,034,758 | A * | 3/1936 | Hicke, Jr. | A61H 15/0085 |
| | | | | 601/113 |
| 2,048,712 | A * | 7/1936 | Schramm | A61H 23/0218 |
| | | | | 601/94 |
| 2,218,443 | A * | 10/1940 | Tweddle | A61H 9/005 |
| | | | | 601/113 |
| 2,258,931 | A * | 10/1941 | Heer | A61H 15/0085 |
| | | | | 601/113 |
| 2,384,427 | A * | 9/1945 | Andis | A61H 15/0078 |
| | | | | 601/125 |
| 2,629,374 | A * | 2/1953 | Acerbi | A61H 15/0085 |
| | | | | 601/130 |
| 3,077,878 | A * | 2/1963 | Baulard-Cogan | A61H 15/0085 |
| | | | | 601/113 |
| 3,385,290 | A * | 5/1968 | Schmidt | A61H 15/0085 |
| | | | | 601/130 |
| 3,994,290 | A * | 11/1976 | Springer | A61H 15/0078 |
| | | | | 601/131 |
| 3,996,929 | A * | 12/1976 | Mabuchi | A61H 15/0078 |
| | | | | 601/124 |
| 4,127,116 | A * | 11/1978 | Pannetier | A61H 15/0085 |
| | | | | 601/125 |
| 4,175,551 | A * | 11/1979 | D'Haenens | A61H 15/0092 |
| | | | | 601/122 |
| 4,432,355 | A * | 2/1984 | Delluc | A46B 13/06 |
| | | | | 15/29 |
| 5,090,402 | A * | 2/1992 | Bazin | A61H 15/02 |
| | | | | 601/131 |
| 5,656,018 | A * | 8/1997 | Tseng | A61H 15/0085 |
| | | | | 601/112 |
| 5,662,593 | A * | 9/1997 | Tillman | A61H 15/0085 |
| | | | | 601/113 |
| 5,690,608 | A * | 11/1997 | Watanabe | A61H 15/0092 |
| | | | | 601/19 |
| 5,769,798 | A * | 6/1998 | Frajdenrajch | A61H 15/0085 |
| | | | | 310/75 D |
| 6,443,915 | B1 * | 9/2002 | Hwang | A61N 1/32 |
| | | | | 601/15 |
| 6,494,849 | B2 * | 12/2002 | Kuo | A61H 15/0078 |
| | | | | 601/112 |
| 2002/0147467 | A1 * | 10/2002 | Bernabei | A61H 7/008 |
| | | | | 607/3 |
| 2002/0198478 | A1 * | 12/2002 | Tsai | A61H 15/0085 |
| | | | | 601/112 |
| 2004/0133134 | A1 * | 7/2004 | Polychronis | A61H 15/0085 |
| | | | | 601/113 |
| 2005/0075591 | A1 * | 4/2005 | Hafemann | A61H 15/0078 |
| | | | | 601/113 |
| 2006/0135319 | A1 * | 6/2006 | Berman | A61H 7/005 |
| | | | | 482/11 |
| 2008/0014011 | A1 * | 1/2008 | Rossen | A45D 34/041 |
| | | | | 401/195 |
| 2008/0183252 | A1 * | 7/2008 | Khen | A61B 18/14 |
| | | | | 607/101 |
| 2008/0221504 | A1 * | 9/2008 | Aghion | A61H 7/008 |
| | | | | 604/20 |
| 2010/0010401 | A1 * | 1/2010 | Tudico | A61H 7/005 |
| | | | | 601/118 |
| 2010/0160841 | A1 * | 6/2010 | Wu | A61H 7/004 |
| | | | | 601/135 |
| 2010/0222719 | A1 * | 9/2010 | Cowie | A61H 7/005 |
| | | | | 601/46 |
| 2011/0009783 | A1 * | 1/2011 | Dverin | A61B 18/14 |
| | | | | 601/137 |
| 2012/0209151 | A1 * | 8/2012 | Zhou | A61H 23/0245 |
| | | | | 601/2 |
| 2013/0046212 | A1 * | 2/2013 | Nichols | A46B 7/04 |
| | | | | 601/18 |
| 2014/0142472 | A1 * | 5/2014 | Giraud | A61H 7/005 |
| | | | | 601/18 |
| 2014/0142480 | A1 * | 5/2014 | Giraud | A61N 1/303 |
| | | | | 601/127 |
| 2014/0288473 | A1 * | 9/2014 | Matsushita | A61H 15/00 |
| | | | | 601/137 |
| 2016/0175185 | A1 * | 6/2016 | Buchner Santos | A61H 15/0085 |
| | | | | 601/113 |
| 2016/0184177 | A1 * | 6/2016 | Caberlotto | A61H 15/0085 |
| | | | | 601/114 |
| 2016/0262973 | A1 * | 9/2016 | Giraud | A61H 15/0078 |
| 2016/0271009 | A1 * | 9/2016 | Giraud | A61H 23/006 |
| 2017/0056685 | A1 * | 3/2017 | Harvey | A61N 5/0616 |
| 2017/0065481 | A1 * | 3/2017 | Matsushita | A61H 7/007 |
| 2017/0189670 | A1 * | 7/2017 | Brunson | A61N 1/303 |
| 2017/0319427 | A1 * | 11/2017 | Udhardt | A61H 15/0085 |
| 2018/0036197 | A1 * | 2/2018 | Khansari | A61H 15/02 |
| 2018/0116903 | A1 * | 5/2018 | Matsushita | A61H 15/00 |
| 2018/0185236 | A1 * | 7/2018 | Levi | A61H 15/02 |
| 2018/0193219 | A1 * | 7/2018 | Hashimoto | A61H 7/007 |
| 2019/0000211 | A1 * | 1/2019 | Planard-Luong | A61N 1/303 |
| 2019/0008718 | A1 * | 1/2019 | Matsushita | A61H 15/0092 |

* cited by examiner

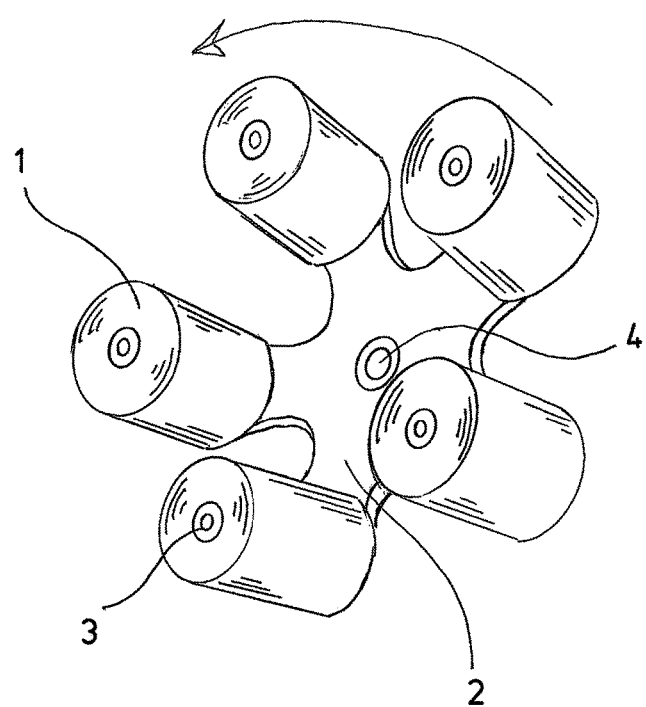

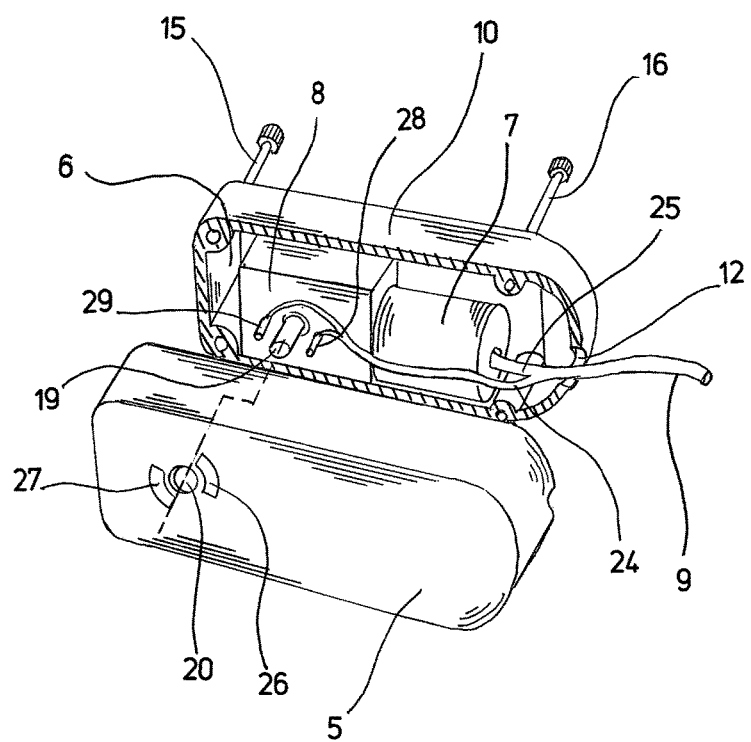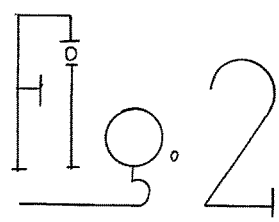

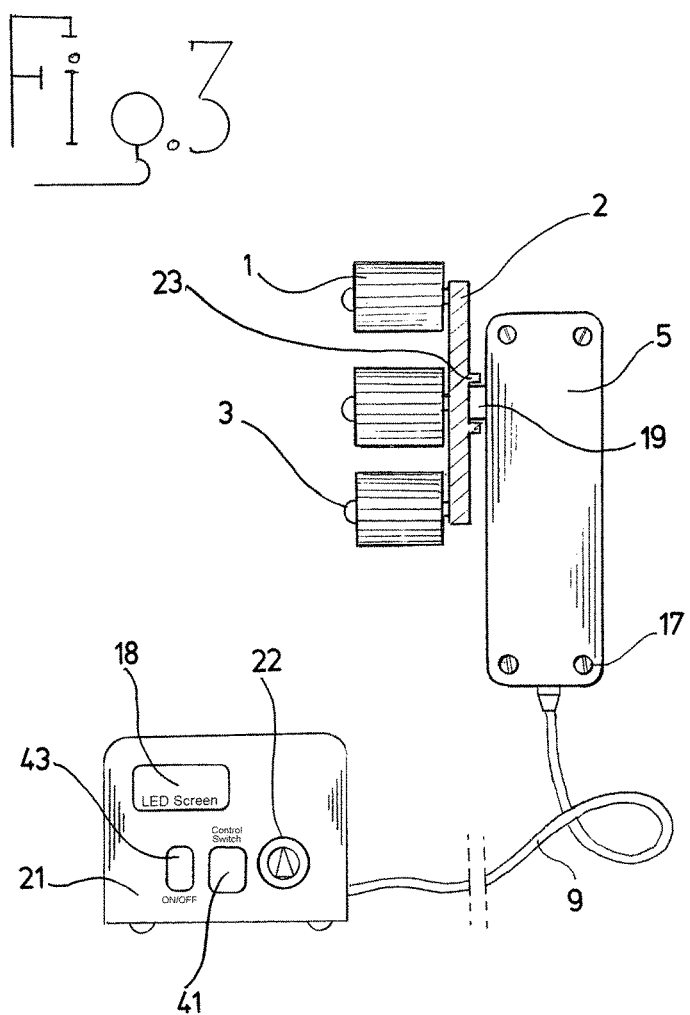

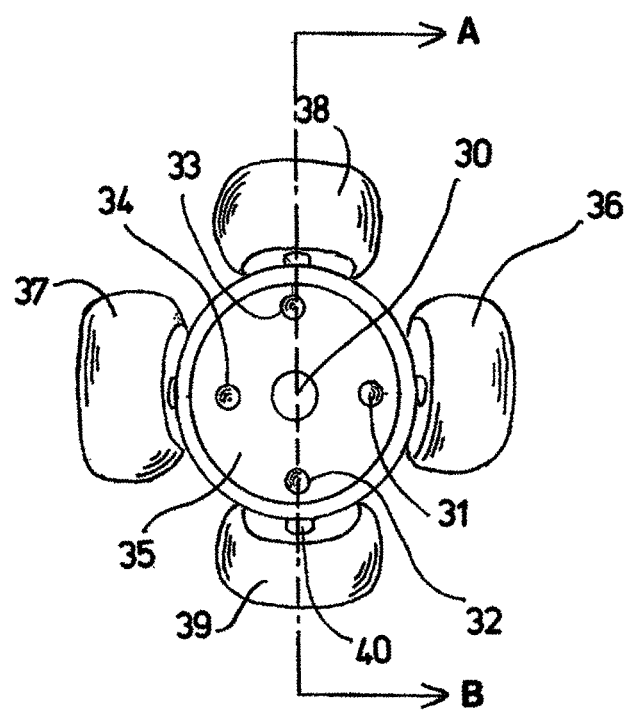
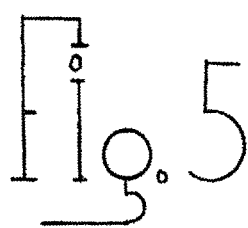

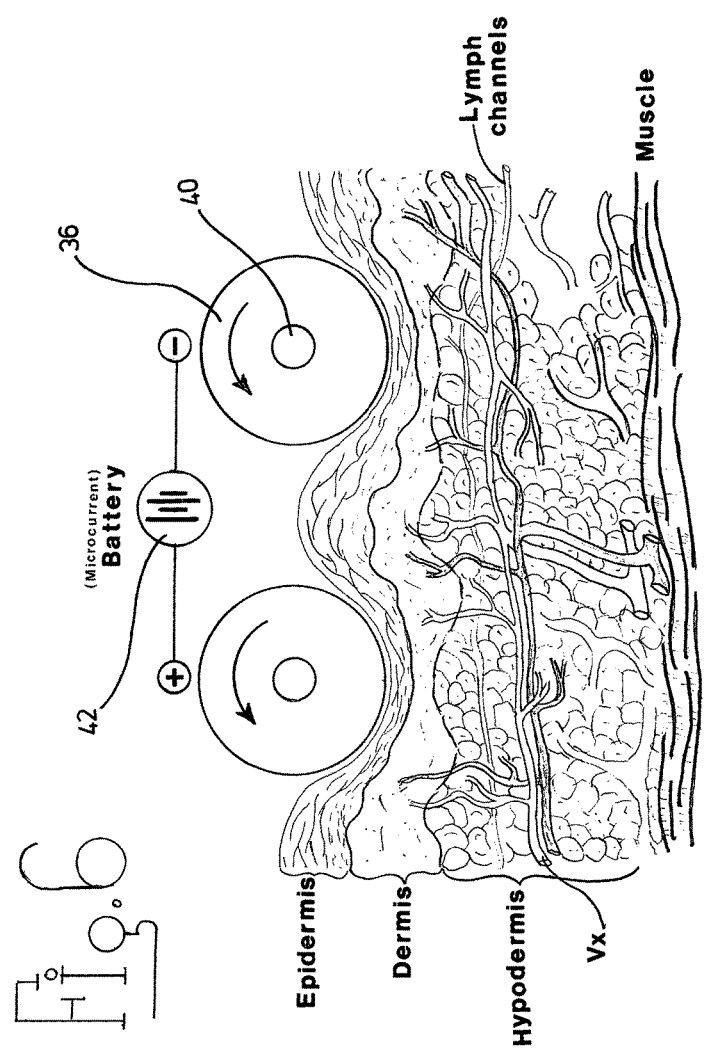

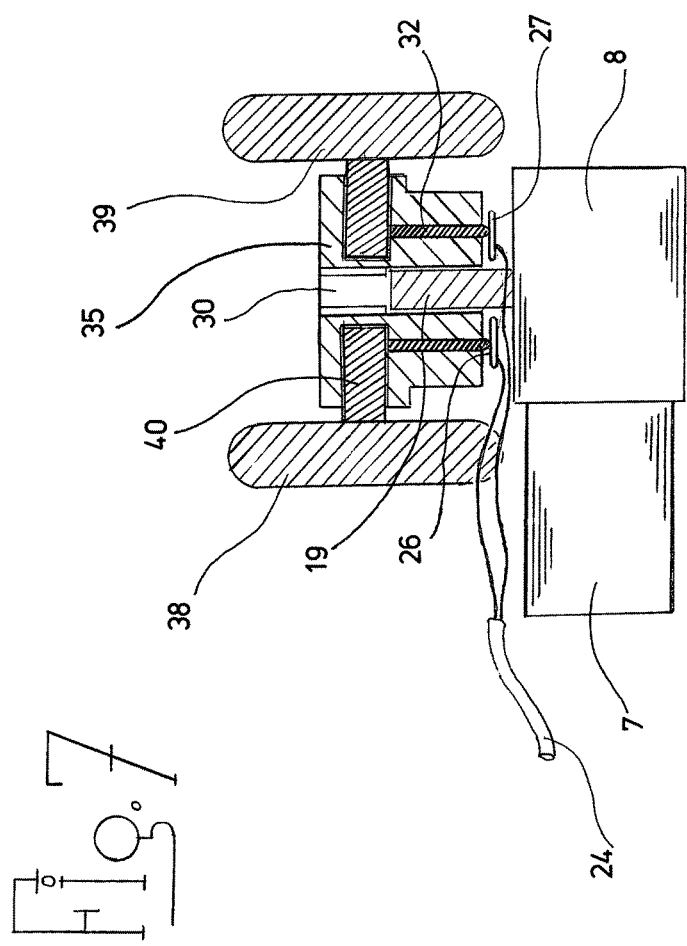

FACIAL ROLLER MASSAGER

FIELD OF THE INVENTION

The present invention relates to a facial skin electrically operated massager and more particularly a vertical roller facial skin massager capable of producing a specific massage motion.

DESCRIPTION OF THE PRIOR ART

Facial skin is the most sensitive part of the human anatomy. People, in general, thrive for a better look using different surgical and medical available technology in order to achieve such purpose.

A plethora of devices have been described in the past, mainly using rotary motion of the massaging ends, which contact the facial skin in a horizontal and circular manner, thereby applying or removing cosmetic products from the facial skin. Traditionally, pressure is applied manually on the skin by the hand of the operator as contrasted to the use of mechanically precise and measured pressure. This is more significant with respect to the face, where more sensitive skin and sharp contours of the face anatomy require gentleness and precision of the massaging act.

The desirable way of regular facial hand massaging includes gentle and firm upward and outward movement of the fingers, which can be used in conjunction with application of various cosmetic preparations that may improve the circulation and tone of the facial skin. It has been a well-established fact that such upward massaging movement is especially desirable since it improves blood and lymphatic circulation of the subcutaneous tissue leading to increased tone of the facial skin and retards wrinkles.

The present disclosure provides an electrically driven massage device capable of reproducing the particular fine movements of the fingers during a facial massage that is improved over the known massage devices.

SUMMARY OF THE INVENTION

A novel mechanical means for massaging the skin of the face in a gentle, soothing, but firm manner using multiple rollers coming in contact with the skin in a vertical circular fashion and rolling upward and outward fashion is disclosed.

According to one embodiment, an electrically driven facial massager applies a firm upward and outward massaging pattern in conjunction with a "thumping" effect at the massaged area which is significantly effective in increasing the local blood and lymphatic circulation.

In particular, the rapid sequential contact of said rollers with the skin provides a "thumping effect" that initially compress the multiple layers of the skin as the roller passes over, milking, and squeezing forward toward draining lymphatic channels, residual lymphatic and extracellular fluid and toxins responsible for puffiness and wrinkles of the facial skin. The squeezing period is followed by a decompression of the layers of the skin as the roller has moved to and adjacent area of the facial skin.

The thumping, compression and decompression effect as described, provides a significant milking effect of the blood vessels and lymphatics drainage channels of the facial skin. The sequence of events is repeated as the next roller moves over and repeat the cycle. In accordance with the foregoing and other objective of the present invention, there is provided a rolling facial massager for improving blood circulation of the facial skin.

In another embodiment of the present invention, electricity conducting rollers convey to the skin safe level of electrical microcurrent in order to deliver medication and cosmological products as a noninvasive transdermal route. Iontophoresis has been used for decades as a process of transporting ionic molecules into the tissues by passage of electric current through the electrolyte solution containing the ionic molecules using suitable electrodes. Electrical energy assists the movement of ions across the stratum corneum according to the basic electrical principle of like charges repel other and opposite charges attracts. The cosmological product is applied under an electrode of the same polarity as the product and the return electrode opposite in charge is placed nearby on the skin surface.

BRIEF DESCRIPTION OF DRAWINGS

The present invention can be easily understood by reading the subsequent detailed description of the preferred embodiment thereof with references made to the accompanying drawings, wherein:

FIG. 1 is a perspective view of roller attached to the rotating base.

FIG. 2 is a perspective view of the opened casing of the motor unit.

FIG. 3 is a side view of the rollers attached to the motor hand unit and power control unit.

FIG. 5 is a top view of the electrical stimulator rollers.

FIG. 6 is a non to scale schematic view of the electrical stimulator rollers acting upon a cross sectional view of facial skin.

FIG. 7 is a sectional view of A B in FIG. 5 showing the electrical connections of the metallic rollers.

DETAILED DESCRIPTION OF THE PREFERRED EMBODIMENT

Figure 4:
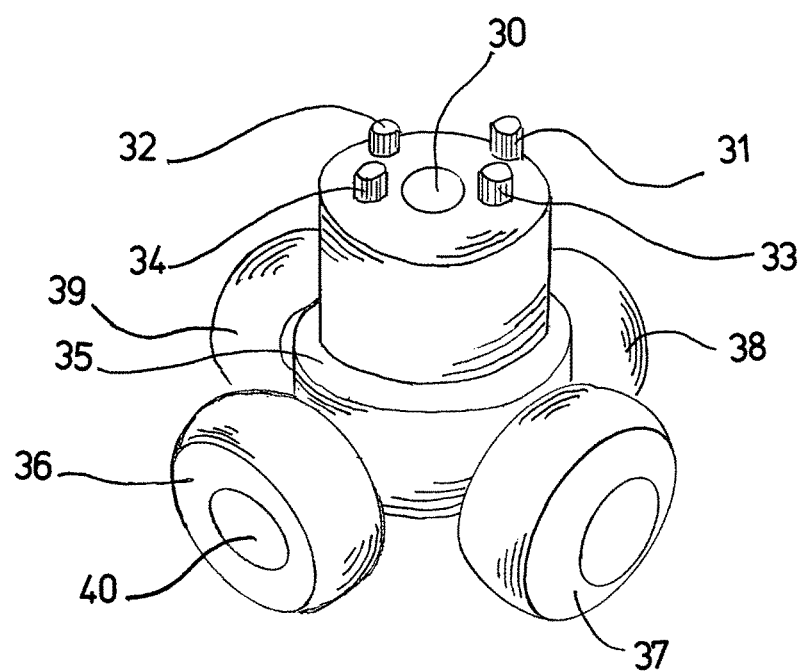
FIG. 4 is a perspective view of the electrical stimulator rollers.

Referring to FIG. 1, rollers 1 are attached to rotating base plate 2. Each roller 1 is capable of freely rotating around its central axis 3, which is firmly attached to rotating base plate 2. Said rotating base plate 2 is firmly affixed to rotating axis 19 (shown in FIG. 2).

Now referring to FIG. 2, gear box 8 situated in the hand-held unit 6 provides a rotating shaft 19 passing through opening 20 of hand-held 6 unit to which, the rotating base plate 2 (shown in FIG. 1) is firmly secured in its center via detachable snapping mechanism 4 (shown in FIG. 1). In a preferred embodiment, rotating base plate 2 has five rollers 1. However, in other embodiments, the number of rollers 1 can vary between two and eight.

Rollers 1 are made of soft silicone or other soft skin friendly material. The rotating base plate 2 rotates in such a manner that allow the roller to roll over the facial skin thereby providing a milking effect that will remove the excessive lymph and extracellular fluid which causes wrinkling of the upper layers of the skin. The circular movement of the rollers 1 is accomplished by holding the hand-held unit 6 so that the rotating base plate 2 (shown in FIG. 1) is vertical to the surface of the skin and the rollers simply rolls over the skin in a sequential manner.

The vertical sequential rotating effect of the rollers provide "thumping" effect as said rollers depress the skin layers, which stimulates superficial skin blood circulation and drain the superficial lymphatic channels as shown in FIG. 6.

Referring to FIG. 3, the circular speed of the rollers is variable and controlled via control unit 21 using speed control knob 22. The motor in the hand-held unit 6 is firmly attached to a planetary gear box 8 providing increased torque and power to the rollers. The electric power to the hand-held unit is provided by the power cord 9. The motor 7 and the gear box 8 are situated in the hand-held unit comprising two halves secured by screws 15 and 16 (shown in FIG. 2).

In a different embodiment of the present invention, the soft rollers and the rotating base are interchangeable with metallic conductive rollers as seen in FIGS. 4 through 7.

Four electrical conductive metallic rollers 36, 37, 38, 39 are vertically attached to central core 35 via central axles 40. Each of the four horizontally situated axles 40 are in electrical continuity with their four respective metallic connectors 31, 32, 33, and 34.

The metallic rollers assembly as shown in FIGS. 4 through 7 are then slidingly attached to the hand-held unit 6 where rotating shaft 19 slides into central opening 30 of central core 35. In doing so, electric contact is established between the metallic pins 31, 32, 33, 34 and the conductive electrical flat contacts 26 and 27 situated around the opening 20 of the hand-held unit cover 5.

The location of said flat contacts 26 and 27 are diametrically opposed around opening 20 in such a way as to allow only two opposite and alternate metallic pins 31 and 34 or 32, and 33 to come in contact with the flat metallic conductive contacts during rotation of the rollers. Furthermore, the flat contacts are in electrical continuity with electrical terminals pins 28 and 29, which receive electrical microcurrent from power supply unit 21 through connecting wires 24 and power cord 9.

The stimulating microcurrent is generated by electronic circuitry located in the power supply unit 21. Said power supply unit comprises speed control knob 22 for controlling the speed of rotation of the rollers and LED information screen 18 for indicating the intensity of the current and main on/off switch 43 for the unit, as well as control switch 41 for microcurrent intensity control.

What is claimed is:

1. Hand held device for facial skin massaging comprising:
   a gearbox having a rotating shaft protruding from said hand held device;
   an electric motor, attached to said gearbox;
   an interchangeable snap-in rotating base having a plurality of rollers attached thereto; and
   control unit box for providing direct current (DC) to said electric motor via a power cord, said interchangeable snap-in rotating base includes a plurality of metallic conductive rollers uniformly disposed along the interchangeable snap-in rotating base; said plurality of metallic conductive rollers has an axis of rotation perpendicular to said rotating shaft so that said plurality of metallic conductive rollers are configured to roll vertically over the skin surface when said interchangeable snap-in rotating base is rotating; and
   a unit cover having an opening with two flat electrical contacts diametrically opposed around said opening; wherein said interchangeable snap-in rotating base further includes a plurality of exposed metallic pins, wherein the plurality of exposed metallic pins comprise an exposed metallic pin for each of said metallic conductive roller, wherein each of the plurality of metallic pins being in electrical continuity with its corresponding metallic conductive roller, whereby two opposed metallic pins of the plurality of metallic pins are alternately in contact with said two flat electrical contacts during rotation of said plurality of metallic conductive rollers.

2. The hand held device of claim 1, wherein the control unit box further comprises:
   a power supply unit for supplying electrical power to said electric motor; and
   a rheostat for adjusting a speed of rotation of said plurality of rollers.

3. The hand held device of claim 2, wherein said power supply unit further comprises electronic circuitry for generating microcurrent to be conveyed to said plurality of metallic conductive rollers.

4. The device of claim 1, wherein the plurality of conductive metallic rollers on the interchangeable snap-in rotating base comprise four to ten conductive metallic rollers.

* * * * *